(12) United States Patent
Godara et al.

(10) Patent No.: US 9,216,053 B2
(45) Date of Patent: Dec. 22, 2015

(54) ELONGATE MEMBER PROVIDING A VARIATION IN RADIOPACITY

(75) Inventors: Neil Godara, Mississauga (CA); Krishan Shah, Mississauga (CA); Amy Lefler, Toronto (CA); Robert Harrison, Hamilton (CA)

(73) Assignee: Avent, Inc., Alpharetta, GA (US)

( * ) Notice: Subject to any disclaimer, the term of this patent is extended or adjusted under 35 U.S.C. 154(b) by 2024 days.

(21) Appl. No.: 11/733,515

(22) Filed: Apr. 10, 2007

(65) Prior Publication Data

US 2007/0203402 A1    Aug. 30, 2007

Related U.S. Application Data

(63) Continuation-in-part of application No. 11/457,697, filed on Jul. 14, 2006, which is a continuation-in-part of application No. 11/105,527, filed on Apr. 14, 2005, now Pat. No. 8,882,755, and a continuation-in-part of (Continued)

(51) Int. Cl.
*A61B 18/12* (2006.01)
*A61B 18/14* (2006.01)
*A61B 19/00* (2006.01)

(52) U.S. Cl.
CPC .............. *A61B 18/1477* (2013.01); *A61B 19/54* (2013.01)

(58) Field of Classification Search
CPC ............... A61B 18/1477; A61B 18/14; A61B 18/1482; A61B 19/54
USPC .................................. 606/41–52; 607/88–94
See application file for complete search history.

(56) References Cited

U.S. PATENT DOCUMENTS

| 4,041,931 A | 8/1977 | Elliott et al. |
| 4,202,349 A | 5/1980 | Jones |
| 4,257,429 A | 3/1981 | Dickhudt et al. |
| 4,419,095 A | 12/1983 | Nebergall et al. |
| 4,447,239 A | 5/1984 | Krutten |
| 4,548,027 A | 10/1985 | Maeoka |
| 4,612,934 A | 9/1986 | Borkan |

(Continued)

FOREIGN PATENT DOCUMENTS

| CA | 1160932 | 1/1984 |
| EP | 0547772 | 6/1993 |

(Continued)

OTHER PUBLICATIONS

International Search Report (PCT/CA2006/001163)—7 pages.

(Continued)

*Primary Examiner* — Aaron Roane
(74) *Attorney, Agent, or Firm* — Dority & Manning, P.A.

(57) ABSTRACT

An elongate member for inserting into a cannula is disclosed. The cannula comprises an electrically insulated region and an electrically exposed conductive region for delivering energy to form a lesion within a patient's body at an intended location relative to the electrically exposed conductive region. The elongate member is structured to cooperatively engage with the cannula at a pre-determined insertion depth and to provide a variation in radiopacity, at a pre-determined position relative to the electrically exposed conductive region, when inserted to the pre-determined insertion depth. The variation in radiopacity provides a visual reference for distinguishing, using fluoroscopic imaging, the intended location of the lesion.

11 Claims, 8 Drawing Sheets

Related U.S. Application Data application No. 10/087,856, filed on Mar. 5, 2002, now Pat. No. 6,896,675, said application No. 11/457,697 is a continuation-in-part of application No. 11/105,490, filed on Apr. 14, 2005, now abandoned, and a continuation-in-part of application No. 10/087,856, filed on Mar. 5, 2002, now Pat. No. 6,896,675, said application No. 11/457,697 is a continuation-in-part of application No. 11/105,524, filed on Apr. 14, 2005, now Pat. No. 7,294,127, and a continuation-in-part of application No. 10/087,856, filed on Mar. 5, 2002, now Pat. No. 6,896,675, said application No. 11/456,697 is a continuation-in-part of application No. 11/381,783, filed on May 5, 2006, now abandoned, and a continuation-in-part of application No. 10/864,410, filed on Jun. 10, 2004, now Pat. No. 7,163,536, and a continuation-in-part of application No. 11/207,707, filed on Aug. 22, 2005, now abandoned, which is a continuation-in-part of application No. 11/079,318, filed on Mar. 15, 2005, now Pat. No. 7,593,778, which is a continuation-in-part of application No. 10/382,836, filed on Mar. 7, 2003, now abandoned, said application No. 11/207,707 is a continuation-in-part of application No. 11/125,247, filed on May 10, 2005, now Pat. No. 7,306,596, which is a continuation-in-part of application No. 10/853,126, filed on May 26, 2004, now abandoned.

(60) Provisional application No. 60/744,518, filed on Apr. 10, 2006, provisional application No. 60/604,348, filed on Aug. 25, 2004, provisional application No. 60/743,511, filed on Mar. 16, 2006, provisional application No. 60/595,559, filed on Jul. 14, 2005, provisional application No. 60/595,560, filed on Jul. 14, 2005.

(56) References Cited

U.S. PATENT DOCUMENTS

| | | | | |
|---|---|---|---|---|
| 4,657,024 | A | 4/1987 | Coneys | |
| 5,191,900 | A | 3/1993 | Mishra | |
| 5,209,749 | A | 5/1993 | Buelna | |
| 5,342,343 | A | 8/1994 | Kitaoka et al. | |
| 5,342,357 | A | 8/1994 | Nardella | |
| 5,397,338 | A | 3/1995 | Grey et al. | |
| 5,429,597 | A | 7/1995 | DeMello et al. | |
| 5,429,617 | A | 7/1995 | Hammersmark et al. | |
| 5,433,739 | A | 7/1995 | Sluijter et al. | |
| 5,458,597 | A * | 10/1995 | Edwards et al. | 606/41 |
| 5,545,193 | A | 8/1996 | Fleischman et al. | |
| 5,571,147 | A | 11/1996 | Sluijter et al. | |
| 5,683,384 | A * | 11/1997 | Gough et al. | 606/41 |
| 5,693,043 | A | 12/1997 | Kittrell et al. | |
| 5,759,174 | A | 6/1998 | Fischell et al. | |
| 5,766,171 | A | 6/1998 | Silvestrini | |
| 5,776,092 | A | 7/1998 | Farin et al. | |
| 5,779,642 | A | 7/1998 | Nightengale | |
| 5,800,428 | A | 9/1998 | Nelson et al. | |
| 5,855,577 | A | 1/1999 | Murphy-Chutorian et al. | |
| 5,895,386 | A | 4/1999 | Odell | |
| 5,951,546 | A | 9/1999 | Lorentzen | |
| 6,002,964 | A | 12/1999 | Feler et al. | |
| 6,056,743 | A | 5/2000 | Ellis et al. | |
| 6,102,886 | A | 8/2000 | Lundquist et al. | |
| 6,104,957 | A | 8/2000 | Alo et al. | |
| 6,126,654 | A | 10/2000 | Giba et al. | |
| 6,129,726 | A | 10/2000 | Edwards | |
| 6,146,380 | A | 11/2000 | Racz et al. | |
| 6,176,857 | B1 | 1/2001 | Ashley | |
| 6,235,000 | B1 | 5/2001 | Milo et al. | |
| 6,251,104 | B1 | 6/2001 | Kesten et al. | |
| 6,277,112 | B1 | 8/2001 | Underwood et al. | |
| 6,280,441 | B1 | 8/2001 | Ryan | |
| 6,306,132 | B1 | 10/2001 | Moorman et al. | |
| 6,315,790 | B1 | 11/2001 | Gerberding et al. | |
| 6,330,478 | B1 * | 12/2001 | Lee et al. | 607/101 |
| 6,355,033 | B1 | 3/2002 | Moorman et al. | |
| 6,379,349 | B1 | 4/2002 | Müller et al. | |
| 6,464,723 | B1 | 10/2002 | Callol | |
| 6,471,700 | B1 | 10/2002 | Burbank et al. | |
| 6,478,793 | B1 | 11/2002 | Cosman et al. | |
| 6,501,992 | B1 | 12/2002 | Belden et al. | |
| 6,562,033 | B2 | 5/2003 | Shah et al. | |
| 6,582,426 | B2 | 6/2003 | Moorman et al. | |
| 6,620,156 | B1 | 9/2003 | Garito | |
| 6,622,731 | B2 | 9/2003 | Daniel | |
| 6,689,127 | B1 * | 2/2004 | Gough et al. | 606/41 |
| 6,726,684 | B1 | 4/2004 | Woloszko | |
| 6,735,474 | B1 | 5/2004 | Loeb et al. | |
| 6,757,565 | B2 | 6/2004 | Sharkey | |
| 6,770,070 | B1 | 8/2004 | Balbierz | |
| 6,773,446 | B1 | 8/2004 | Dwyer et al. | |
| 6,780,181 | B2 | 8/2004 | Kroll et al. | |
| 6,847,849 | B2 | 1/2005 | Mamo et al. | |
| 6,893,421 | B1 * | 5/2005 | Larson et al. | 604/164.01 |
| 6,902,526 | B2 | 6/2005 | Katzman | |
| 6,932,811 | B2 | 8/2005 | Hooven | |
| 6,966,902 | B2 | 11/2005 | Tsugita et al. | |
| 6,974,454 | B2 | 12/2005 | Hooven | |
| 7,097,641 | B1 | 8/2006 | Arless et al. | |
| 7,175,631 | B2 | 2/2007 | Wilson et al. | |
| 7,270,658 | B2 | 9/2007 | Woloszko et al. | |
| 7,462,178 | B2 | 12/2008 | Woloszko et al. | |
| 2001/0000041 | A1 | 3/2001 | Selmon et al. | |
| 2001/0027309 | A1 | 10/2001 | Elsberry | |
| 2001/0056280 | A1 | 12/2001 | Underwood | |
| 2002/0026127 | A1 | 2/2002 | Balbierz | |
| 2002/0032440 | A1 | 3/2002 | Hooven | |
| 2002/0049437 | A1 | 4/2002 | Silvestrini | |
| 2002/0072739 | A1 | 6/2002 | Lee | |
| 2002/0091384 | A1 | 7/2002 | Godinho de Queiroz e Melo | |
| 2002/0103484 | A1 | 8/2002 | Hooven | |
| 2002/0120260 | A1 | 8/2002 | Morris et al. | |
| 2002/0147485 | A1 | 10/2002 | Mamo et al. | |
| 2002/0193781 | A1 | 12/2002 | Loeb | |
| 2003/0014047 | A1 | 1/2003 | Woloszko | |
| 2003/0015707 | A1 | 1/2003 | Bosco | |
| 2003/0023239 | A1 | 1/2003 | Burbank et al. | |
| 2003/0032936 | A1 | 2/2003 | Lederman | |
| 2003/0040742 | A1 | 2/2003 | Underwood | |
| 2003/0093007 | A1 | 5/2003 | Wood | |
| 2003/0100895 | A1 | 5/2003 | Simpson et al. | |
| 2003/0109870 | A1 | 6/2003 | Lee | |
| 2003/0120195 | A1 | 6/2003 | Milo et al. | |
| 2003/0125729 | A1 | 7/2003 | Hooven | |
| 2003/0153906 | A1 | 8/2003 | Sharkey | |
| 2003/0158545 | A1 | 8/2003 | Hovda et al. | |
| 2003/0195593 | A1 * | 10/2003 | Ingle et al. | 607/99 |
| 2003/0212394 | A1 * | 11/2003 | Pearson et al. | 606/41 |
| 2003/0212395 | A1 | 11/2003 | Woloszko | |
| 2003/0233125 | A1 | 12/2003 | Kaplan et al. | |
| 2004/0054366 | A1 | 3/2004 | Davidson et al. | |
| 2004/0082942 | A1 | 4/2004 | Katzman | |
| 2004/0106891 | A1 | 6/2004 | Langan et al. | |
| 2004/0187875 | A1 | 9/2004 | He et al. | |
| 2004/0199161 | A1 | 10/2004 | Truckai et al. | |
| 2004/0215287 | A1 | 10/2004 | Swoyer et al. | |
| 2004/0249373 | A1 | 12/2004 | Gronemeyer et al. | |
| 2004/0267203 | A1 | 12/2004 | Potter et al. | |
| 2004/0267254 | A1 | 12/2004 | Manzo | |
| 2005/0033372 | A1 | 2/2005 | Gerber et al. | |
| 2005/0049570 | A1 * | 3/2005 | Chin et al. | 604/500 |
| 2005/0085806 | A1 | 4/2005 | Auge, II et al. | |
| 2005/0096718 | A1 | 5/2005 | Gerber et al. | |
| 2005/0177209 | A1 | 8/2005 | Leung et al. | |
| 2005/0177211 | A1 | 8/2005 | Leung et al. | |
| 2005/0187542 | A1 | 8/2005 | Auge | |

(56) References Cited

U.S. PATENT DOCUMENTS

| | | | |
|---|---|---|---|
| 2005/0240238 | A1 | 10/2005 | Mamo |
| 2006/0020297 | A1 | 1/2006 | Gerber et al. |
| 2006/0025763 | A1 | 2/2006 | Nelson et al. |

FOREIGN PATENT DOCUMENTS

| | | |
|---|---|---|
| EP | 0642800 | 3/1995 |
| EP | 0651661 | 6/2000 |
| EP | 0865768 | 2/2003 |
| EP | 1344497 | 9/2003 |
| WO | 81/03272 | 11/1981 |
| WO | 94/02077 | 2/1994 |
| WO | 94/09560 | 4/1994 |
| WO | 94/22384 | 10/1994 |
| WO | 94/24948 | 11/1994 |
| WO | 95/10318 | 4/1995 |
| WO | 95/10320 | 4/1995 |
| WO | 95/10327 | 4/1995 |
| WO | 95/21578 | 8/1995 |
| WO | 96/39967 | 12/1996 |
| WO | 97/06739 | 2/1997 |
| WO | 97/06855 | 2/1997 |
| WO | 97/24074 | 7/1997 |
| WO | 98/19613 | 5/1998 |
| WO | 98/27879 | 7/1998 |
| WO | 98/31290 | 7/1998 |
| WO | 98/58747 | 12/1998 |
| WO | 99/42037 | 8/1999 |
| WO | 99/43263 | 9/1999 |
| WO | WO9948548 A1 | 9/1999 |
| WO | WO0145579 | 12/2000 |
| WO | WO0170114 A1 | 8/2001 |
| WO | 01/67975 | 9/2001 |
| WO | 01/74251 | 10/2001 |
| WO | 01/80724 | 11/2001 |
| WO | 02/45609 | 6/2002 |
| WO | 03/037162 | 5/2003 |
| WO | 03/065917 | 8/2003 |
| WO | 03/103522 | 12/2003 |

OTHER PUBLICATIONS

International Search Report (PCT/CA2006/000229)—4 pages.
Buijs et al., "Radiofrequency Treatment of Sacroiliac Joint-Related Pain Aimed at the First Three Sacral Dorsal Raml: A Minimal Approach", Pain Clinic, 16(2):139-146, 2004.
Jiang et al., "Comparison Between Radiofrequency Coagulation Plus Small Needle Knife and Single Method in Treatment of Sacrolumbar Pain", Chinese Journal of Clinical Rehabilitation, 7(20):2844-2845, 2003.
Plancarte et al., "Radiofrequency Procedures for Sacral and Pelvic Region Pain", Pain Practice 2(3):248-249, 2002.
Fukui et al., "Successful Relief of Hip Joint Pain by Percutaneous Radiofrequency Nerve Thermocoagulation in a Patient with Contraindictions for Hip Arthroplasty", J. Anesth., 15(3):173-175, 2001.
Cohen et al., "Pulsed Radiofrequency as a Treatment for Groin Pain and Orchialgia", Urology, 61(3):645, 2003.
Kawaguchi et al., "Percutaneous Radiofrequency Lesioning of Sensory Branches of the Obturator and Femoral Nerves for the Treatment of Hip Joint Pain", Reg Anesth Pain Med. 26(6):578-581, 2001.
Akatov et al., "Percutaneous Radiofrequency Destruction of the Obturator Nerve for Treatment of Pain Caused by Coxarthrosis", Stereotact Funct Neurosurg. 61(1-4 Pt 2):278-280, 1997.
Ferrante et al., "Radiofrequency Sacroiliac Joint Denervation for Sacroiliac Syndrome", Reg Anesth Pain Med 26(2):137-142, 2001.
Gopalani et al., "A Novel Technique for Treating Nonsurgical Hip Pain with Radiofrequency Lesioning of the Sensory Branches of the Obturator and Femoral Nerves: A Case Report", Archives of Physical Medicine and Rehabilitation, 84(9):E23, 2003.
Pino et al., "Morphologic Analysis of Bipolar Radiofrequency Lesions: Implications for Treatment of the Sacroiliac Joint", Reg Anesth Pain Med. 30(4):335-338, 2005.

Yin et al., "Sensory Stimulatin-Guided Sacroiliac Joint Radiofrequency Neurotomy: Technique Based on Neuroanatomy of the Dorsal Sacral Plexus", Spine, 28(20):2419-2425, 2003.
Ahadian, "Pulsed Radiofrequency Neruotomy: Advances in Pain Medicine", Curr Pain Headache Rep, 8(1):34-40, 2004.
Gevargez et al., "CT-Guided Percutaneous Radiofrequency Denervation of the Sacroiliac Joint", Eur Radiol, 12(6):1360-1365, 2002.
Anis et al., "Use of Radio-Frequency Ablation for the Palliative Treatment of Sacral Chordoma", AJNR, 25(9):1589-1591, 2004.
Conaghan et al., "Sacral Nerve Stimulation can be Successful in Patients with Ultrasound Evidence of External Anal Sphincter Disruption", Diseases of the Colon and Rectum, 48(8):1610-1614, 2005.
Kirsch et al., "Proton Radiotherapy for Hodgkin's Disease in the Sacrum", Lancet Oncology, 6(7):532:533, 2005.
Leng et al., "How Sacral Nerve Stimulation Neuromodulation Works", Urol Clin North Am., 32(1):11-18, 2005.
Kirkham et al., "Neuromodulation Through Sacral Nerve Roots 2 to 4 with a Finetech-Brindley Sacral Posterior and Anterior Root Stimulator", Spinal Cord, 40(6):272-281, 2002.
Simon, "Sacroiliac Joint Injection and Low Back Pain", Interventional Pain Management, 535-539, 2001.
Kline et al., "Radiofrequency Techniques in Clinical Practice", Interventional Pain Management 243-290, 2001.
Cole et al., "The Sacroiliac Joint: A Functional Approach", Critical Reviews in Physical and Rehabilitation Medicine, 8(1&2):125-152, 1996.
Atlihan et al., "Anatomy of the Anterior Sacroiliac Joint with Reference to Lumbosacral Nerves", Clinical Orthopaedics and Related Research, 376:2360241, 2000.
Calvillo et al., "Anatomy and Pathophysiology of the Sacroiliac Joint", Current Review of Pain, 4:356-261, 2000.
Davies et al., "Radiofrequency Treatment in the United States", Pain Practice 2(3):192-194, 2000.
Ebraheim et al., "Anatomic Considerations for Posterior Approach to the Sacroiliac Joint", Spine, 21(23):2709-2712, 1996.
Fortin et al., "Three Pathways Between the Sacroiliac Joint and Neural Structures", Am J Neuroradiol., 20:1429-1434, 1999.
Fortin et al., "Sacroiliac Joint Innervation and Pain", The American Journal of Orthopedics, 28:68-90, 1999.
Liguoro et al., "The Posterior Sacral Foramina: An Anatomical Study", J. Anat, 195:301-304, 1999.
Murata et al., "Origin and Pathway of Sensory Nerve Fibers to the Ventral and Dorsal Sides of the Sacroiliac Joint in Rats", Journal of Orthopaedic Research, 19:379-383, 2001.
Prithvi et al., "The Current Status of the Practice of Radiofrequency in the World", Pain Practice, 2(3):176-179, 2002.
Slipman et al., "Sacroiliac Joint Syndrome", Pain Physician, 4(2):143-152, 2001.
Van Zundert et al., "Application of Radiofrequency Treatment in Practical Pain Management: State of the Art", Pain Practice, 2(3):269-278, 2002.
Cohen et al., "Lateral Branch Blocks as a Treatment for Sacroiliac Joint Pain: A Pilot Study", Regional Anesthesia Pain Medicine, 28(2):113-119, 2003.
Valleylab-RF Pain Management System, Sep. 16, 2004, http://www.valleylab.com/static/pain/products-generator.html.
Bogduk N, Macintosh J, Marsland A. "Technical Limitations to the Efficacy of Radiofrequency Neurotomy for Spinal Pain". Neurosurgery 20(4):529-535, 1987.
Lord SM, Barnsley L, Bogduk N. "Percutaneous Radiofrequency Neurotomy in the Treatment of cervical Zygapophysial Joint Pain: A Caution". Neurosurgery 36(4):732-739, 1995.
Dreyfuss P, Rogers CJ. "Radiofrequency Neurotomy of the Zygapophyseal and Sacroiliac Joints". Pain Procedures 2:395-420, 2000.
Lau P, Mercer S, Govind J, Bogduk N. "The Surgical Anatomy of Lumbar Medial Branch Neurotomy (Facet Denervation)". Pain Medicine 5(3):289-298, 2004.
Deer T. "Injections for the Diagnosis and Treatment of Spinal Pain". American Society of Anesthesiologists 32(6):53-69, 2004.

(56) References Cited

OTHER PUBLICATIONS

Lord SM, Barnsley L, Wallis BJ, McDonald GJ, Bogduk N. "Percutaneous Radio-Frequency Neurotomy for Chronic Cervical Zygapophyseal-Joint Pain". New England Journal of Medicine 335(23):1721-1726. 1996.

Hooten WM, Martin DP, Duntoon MA. "Radiofrequency Neurotomy for Low Back Pain: Evidence-Based Procedural Guidelines". Pain Medicine 6(2):129-138, 2005.

Dreyfuss P, Halbrook B, Pauza K, Joshi A, McLarty J, Bogduk N. "Lumbar Radiofrequency Neurotomy for Chronic Zygapophyseal Joint Pain: A Pilot Study Using Dual Medial Branch Blocks". ISIS Scientific Newsletter 3(2):13-30, 1999.

Baylis Medical Company Inc. "Technology Notes—RF Lesion Size in Relation to Cannula Gauge". 2005.

Baylis Medical Company Inc. "Baylis Medical Company—Radiopaque Cannula". 2005.

Curatolo M, Reiz S. "Re: Niemisto L, Kalso E, Malmivaara A, et al. Radiofrequency denervation for neck and back pain: a systematic review within the framework of the cochrane collaboration back review group. Spine 2003;28:1877-88". Spine 30(2):263-268, 2005.

\* cited by examiner

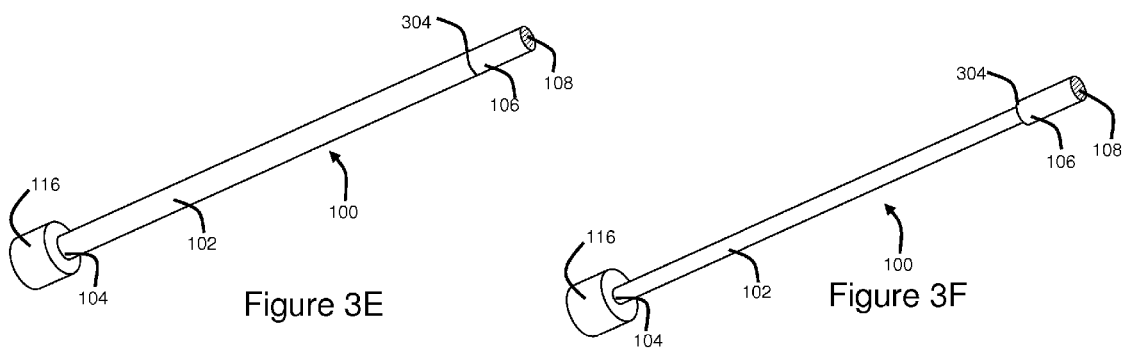

ELONGATE MEMBER PROVIDING A VARIATION IN RADIOPACITY

CROSS REFERENCES TO RELATED APPLICATIONS

This application claims priority from U.S. Provisional Patent Application 60/744,518 (filed on Apr. 10, 2006), and is a continuation-in-part of U.S. patent application Ser. No. 11/457,697 (filed on Jul. 14, 2006). U.S. patent application Ser. No. 11/457,697 is a continuation-in-part of U.S. patent application Ser. No. 11/105,527 (filed on Apr. 14, 2005), Ser. No. 11/105,490 (filed on Apr. 14, 2005), and Ser. No. 11/105,524 (filed on Apr. 14, 2005), all of which claim the benefit of U.S. Provisional Patent Application 60/604,348 (filed on Aug. 25, 2004), and are continuations-in-part of U.S. patent application Ser. No. 10/087,856 (filed on Mar. 5, 2002), now U.S. Pat. No. 6,896,675. U.S. patent application Ser. No. 11/457,697 is also a continuation-in-part of U.S. patent application Ser. No. 11/381,783 (filed on May 5, 2006), and a continuation-in-part of U.S. patent application Ser. No. 10/864,410 (filed on Jun. 10, 2004), and a continuation-in-part of U.S. patent application Ser. No. 11/207,707 (filed on Aug. 22, 2005). U.S. patent application Ser. No. 11/207,707 is a continuation-in-part of U.S. patent application Ser. No. 11/079,318 (filed on Mar. 15, 2005) which is a continuation-in-part of U.S. patent application Ser. No. 10/382,836 (filed on Mar. 7, 2003). U.S. patent application Ser. No. 11/207,707 is also a continuation-in-part of U.S. patent application Ser. No. 11/125,247 (filed on May 10, 2005), which is a continuation-in-part of Ser. No. 10/853,126 (filed on May 26, 2004). U.S. patent application Ser. No. 11/457,697 also claims the benefit of U.S. Provisional Patent Application 60/743,511 (filed on Mar. 16, 2006), 60/595,559 (filed on Jul. 14, 2005), 60/595,560 (filed on Jul. 14, 2005), and 60/744,518 (filed on Apr. 10, 2006). All of the aforementioned patents and applications are incorporated herein by reference, in their entirety.

TECHNICAL FIELD

The invention relates to devices used in electrosurgical procedures. More specifically, the invention relates to devices for visualizing a location of lesion formation.

BACKGROUND OF THE ART

Electrosurgical apparatuses often include a cannula having an electrically insulated region and an electrically exposed conductive region for delivering energy to a tissue to form a lesion, and an elongate member, for example a stylet, for inserting into and occluding the lumen of the cannula. Alternatively, as described in U.S. Ser. No. 10/274,074 (US 2003/0093007 "Wood"), the stylet may provide a means for cauterizing tissue in addition to the means for cauterizing tissue associated with the cannula, and imaging enhancers may be placed on the stylet to assist in visualizing an apparatus.

In some procedures, fluoroscopy is used in order to visualize the cannula when it is inside a patient's body. However, when energy is delivered from a cannula to form a lesion in the body, the lesion generally does not form at the distal end of the cannula. Rather, the lesion forms around the entire electrically exposed conductive region of the cannula. Furthermore, in apparatuses which are cooled, the lesion may form away from the distal end of the cannula, and may not contact the electrically exposed conductive region of the cannula at all. In addition, when a radiopaque marker is affixed to the distal end of a cannula, the shape of the distal end is modified, which may require that extra force be applied when the apparatus is inserted into the patient's body.

Thus, it would be beneficial to provide an apparatus that provides a visual reference indicating where a lesion will form within the body, and which does not interfere with the insertion of the apparatus into the patient's body.

BRIEF DESCRIPTION OF THE DRAWINGS

In order that the invention may be readily understood, embodiments of the invention are illustrated by way of examples in the accompanying drawings, in which:

FIGS. 3A-3F are perspective views of various embodiments of elongate members of the present invention;

DETAILED DESCRIPTION

Figure 1:
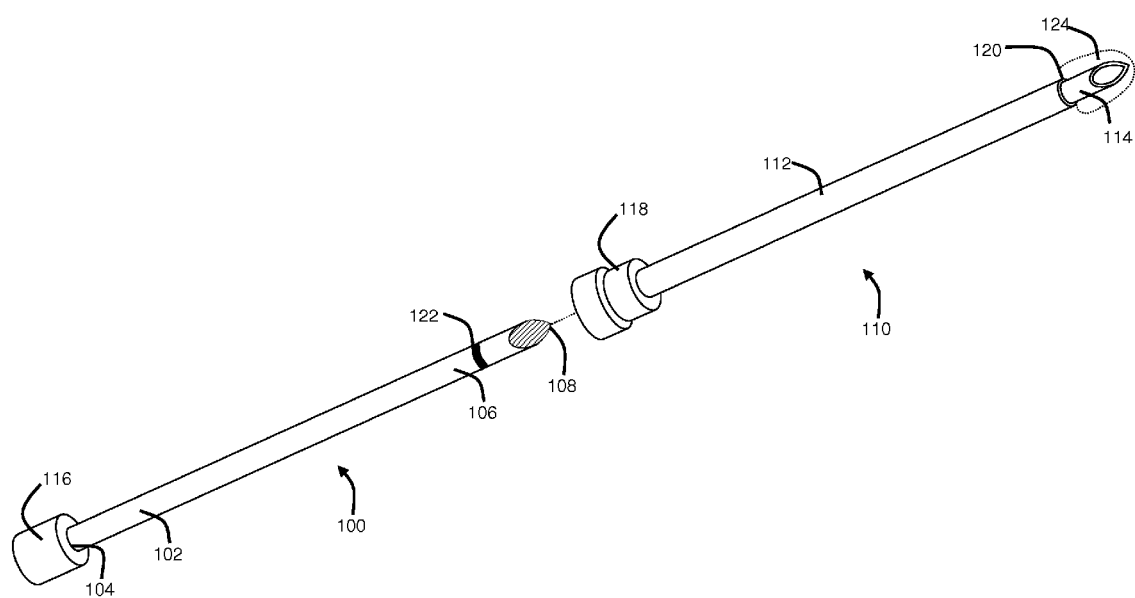
FIG. 1 is a perspective view of an embodiment of an elongate member of the present invention shown adjacent a cannula.

In one broad aspect, embodiments of the present invention comprise an elongate member for inserting into a cannula. The cannula comprises an electrically insulated region and an electrically exposed conductive region for delivering energy to form a lesion within a patient's body at an intended location relative to the electrically exposed conductive region. The elongate member is structured to cooperatively engage with the cannula at a pre-determined insertion depth, and to provide a variation in radiopacity at a pre-determined position relative to the electrically exposed conductive region when inserted to the pre-determined insertion depth. The variation in radiopacity provides a visual reference for distinguishing, using fluoroscopic imaging, the intended location of the lesion.

In a further broad aspect, embodiments of the present invention comprise an elongate member for inserting into a cannula. The cannula comprises an electrically insulated region and an electrically exposed conductive region for delivering energy to form a lesion within a patient's body at an intended location relative to the electrically exposed conductive region. The radiopacity of the elongate member varies at a pre-determined region of the elongate member, such that when the elongate member is inserted into the cannula to a predetermined insertion depth, the pre-determined region substantially longitudinally aligns with a distal end of the electrically insulated region. The variation in radiopacity provides a visual reference for distinguishing, using fluoroscopic imaging, the intended location of the lesion.

In a further broad aspect, embodiments of the present invention comprise a kit. The kit comprises a cannula and an elongate member for inserting into the cannula. The cannula comprises an electrically insulated region and an electrically exposed conductive region for delivering energy to form a lesion within a patient's body at an intended location relative to the electrically exposed conductive region. The elongate member is structured to cooperatively engage with the cannula at a pre-determined insertion depth and to provide a variation in radiopacity at a pre-determined position relative to the electrically exposed conductive region when inserted to the pre-determined insertion depth. The variation in radiopacity provides a visual reference for distinguishing, using fluoroscopic imaging, the intended location of the lesion.

In a further broad aspect, embodiments of the present invention comprise a method for positioning an electrosurgical apparatus. The apparatus comprises a cannula and an elongate member for inserting into the cannula. The cannula comprises an electrically insulated region, and an electrically exposed conductive region for delivering energy to form a lesion at a target site within a patient's body. The elongate member is structured to cooperatively engage with the cannula at a pre-determined insertion depth, and to provide a variation in radiopacity at a pre-determined position relative to the electrically exposed conductive region when inserted to the pre-determined insertion depth. The method comprises the steps of: inserting the cannula to a position near a target site in the patient's body; inserting the elongate member into the cannula; determining the location of the lesion to be made by visualizing the location of the variation in radiopacity; and, responsive to determining the location of the lesion to be made, moving the apparatus, if necessary, to position the electrically exposed conductive region such that at least a portion of the target site is located within the location of lesion to be made.

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring to FIG. 1, an embodiment of an elongate member 100 of the present invention is shown. Elongate member 100 comprises a proximal region 102 ending in proximal end 104, and a distal region 106 ending in distal end 108. Elongate member 100 is sized to be inserted into a cannula. An embodiment of a cannula suitable for use with an elongate member of the present invention will presently be described; however, it is to be noted that elongate member 100 is not limited to use with any particular cannula. A cannula 110 suitable for use with elongate member 100 is shown in FIG. 1. Cannula 110 comprises an electrically insulated region 112, and an electrically exposed conductive region 114. In use, cannula 110 may be percutaneously inserted into a patient's body, and may be connected to a source of energy, for example a radiofrequency generator. Cannula 110 may be connected to the source of energy directly, for example via a wire or cable, or indirectly, for example via a probe inserted into the cannula. Energy is delivered from electrically exposed conductive region 114 to form a lesion at an intended location in the patient's body. The intended location of the lesion relative to electrically exposed conductive region 114 may vary depending on the structure of electrically exposed conductive region 114. In the embodiment of FIG. 1, wherein electrically exposed conductive region 114 is substantially elongate, a substantially ovoid lesion 124 will form around the electrically exposed conductive region.

Figure 2:
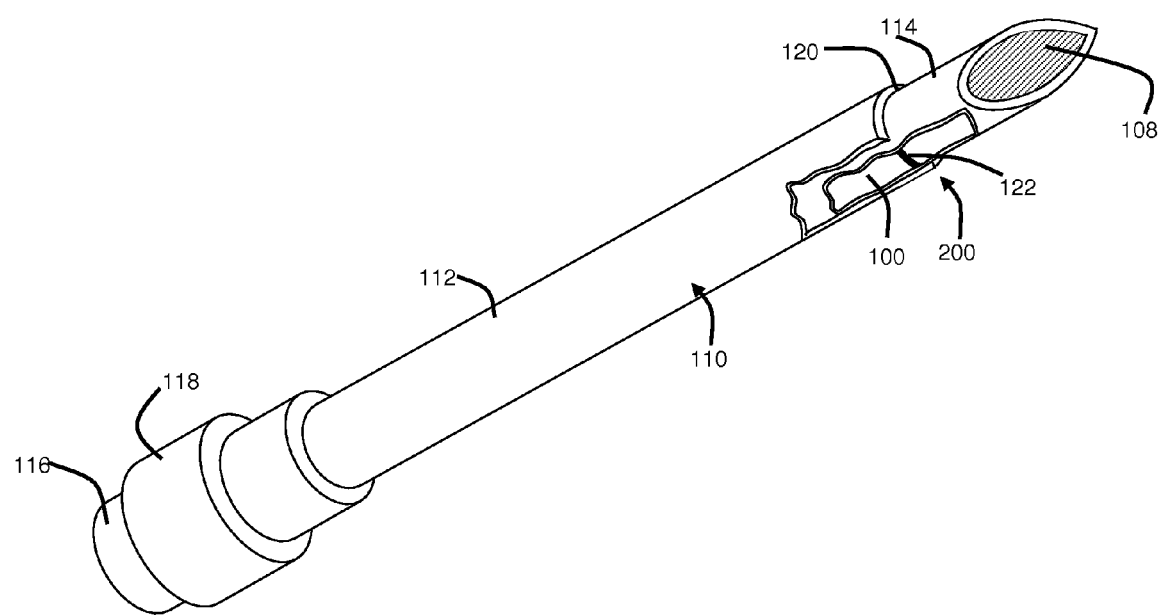
FIG. 2 is a perspective cut-away view of a cannula with an embodiment an elongate member of the present invention inserted into the cannula.

Elongate member 100 is structured to cooperatively engage with cannula 110 at a predetermined insertion depth. That is, elongate member 100 is structured to be inserted into cannula 110 such that at a particular point during insertion, elongate member 100 and cannula 110 will cooperatively engage to resist further insertion, or to indicate to the user that the pre-determined insertion depth has been reached. In the embodiment of FIGS. 1 and 2, the cooperative engagement is provided by a hub 116 at proximal end 104 of elongate member 100, which will contact and substantially abut with a hub 118 at the proximal end of cannula 110, and prevent further insertion. Hub 116 may be manufactured from ABS (acrylonitrile butadiene styrene) or a similar material, and may be attached to elongate member 100 using various methods, including but not limited to insert molding, gluing and other forms of bonding.

Elongate member 100 is structured to provide a variation in radiopacity at a predetermined position relative to electrically exposed conductive region 114 when inserted to the predetermined insertion depth. In other words, elongate member 100 is structured such that, when inserted into cannula 110 to the predetermined insertion depth, there will be a visible (using fluoroscopic imaging, for example) change in radiopacity of the combined apparatus (comprising cannula 110 and elongate member 100) at a predetermined position relative to electrically exposed conductive region 114. The structure providing this variation in radiopacity may be referred to as a means for providing a variation in radiopacity. The variation in radiopacity may be provided in numerous ways, as will be described hereinbelow. In addition, more than one predetermined position relative to electrically exposed conductive region 114 may be provided to identify different intended locations of a lesion to be formed depending on the particular application.

It should be noted that fluoroscopic imaging, similar to other forms of X-ray imaging, typically produces a flat, two dimensional image, showing the cumulative radiopacity of any structures present along a given line between the X-ray source and the image recording plane. Thus, when visualizing the combined apparatus described herein under fluoroscopic imaging, the image will show the cumulative radiopacity of both elongate member 100 as well as cannula 110. Therefore, although the embodiments of the present invention describe structural variations on elongate member 100 that provide the variation in radiopacity, the predetermined position, i.e. the location along the combined apparatus at which the change in radiopacity is visible, will be described with reference to the locations along cannula 110 at which this variation in radiopacity is visible under two-dimensional fluoroscopic imaging.

For example, referring to FIG. 2, when elongate member 100 is inserted to the pre-determined insertion depth, the predetermined position 200, at which the variation in radiopacity of the combined apparatus is provided, is at the distal end 120 of the electrically insulated region 112. As mentioned hereinabove, in the embodiments of FIGS. 1 and 2, lesion 124 may form substantially around electrically exposed conductive region 114. Thus, if the predetermined position 200 is at distal end 120 of electrically insulated region 112, when elongate member 100 and cannula 110 are viewed under fluoroscopy, the variation in radiopacity at predetermined position 200 will provide a visual reference for distinguishing the intended location of the lesion. More specifically, the variation in radiopacity at predetermined position 200 will provide a visual reference aligned with the proximal-most region of the lesion. It is to be noted that, although the variation in radiopacity provides a visual reference for distinguishing the intended location of the lesion, it is not necessary for elongate member 100 to be in contact with the patient's body at the intended location of the lesion. That is, in some embodiments, the means for providing the variation in radiopacity will be located within the cannula lumen when the elongate member is inserted to the pre-determined insertion depth, and thus the elongate member and/or the means for providing the variation in radiopacity may not contact the patient's body at the intended location of the lesion; however, when viewed under fluoroscopy, the variation in radiopacity will provide a visual reference at the intended location of the lesion.

In the embodiments of FIGS. 1 and 2, the variation in radiopacity is provided by a radiopaque marker 122 positioned to substantially longitudinally align with a distal end 120 of electrically insulated region 112 of cannula 110 when elongate member 100 is inserted to the predetermined insertion depth. Radiopaque marker 122 may be any addition of material to elongate member 100, which, when inserted into cannula 110 and viewed under fluoroscopy, will appear enhanced with respect to the remainder of the combined apparatus. In the context of the present disclosure, 'enhanced' refers to increased radiopacity, which typically appears darker on a fluoroscopic image. In contrast, 'diminished intensity', in the context of the present disclosure, refers to reduced radiopacity, which typically appears brighter on a fluoroscopic image. For example, radiopaque marker 122 may be a band of a high density metal or alloy such as platinum, iridium, gold, silver or tantalum or alloys or combinations thereof. Such materials are highly visible under fluoroscopic imaging and are therefore visible even at minimal thicknesses. Radiopaque marker 122 may completely circumscribe elongate member 100, as shown in the embodiment of FIGS. 1 and 2, or it may only partially circumscribe elongate member 100. For example, in some embodiments (not shown), radiopaque marker 122 may only traverse 180° of the circumference of elongate member 100.

Radiopaque marker 122 may be laser welded to elongate member 100, thus improving the heat resistance of the band-to-member bond. Alternatively, radiopaque marker 122 may be applied using any other suitable technique, including but not limited to vapor deposition, ion implantation, dip coating, metal plating, welding, soldering, gluing, and electro plating. In addition, in embodiments wherein radiopaque marker 122 is manufactured from a material such as platinum iridium, radiopaque marker 122 may be fused onto elongate member 100.

Radiopaque marker 122 may be of various widths, wherein 'width' refers to the distance between a proximal edge and a distal edge of radiopaque marker 122. For example, in some embodiments, radiopaque marker 122 may have a width of between about 1 mm and about 2 mm (approximately 0.04-0.08 inches), more specifically between about 1.2 and about 1.3 mm (approximately 0.045-0.055 inches).

In addition to the band shown in FIGS. 1 and 2, radiopaque markers of various shapes and patterns may be applied to elongate member 100 by, for example, the use of various masking techniques.

Figure 3A:
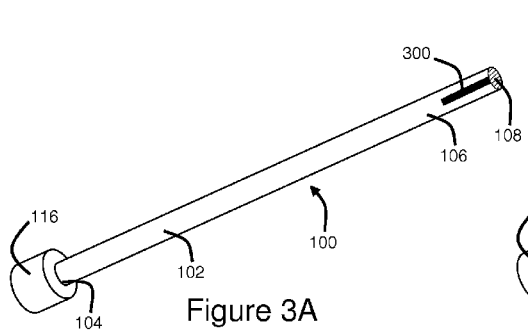

In an alternate embodiment, as shown in FIG. 3A, the variation in radiopacity is provided by a radiopaque marker 300 which may run parallel to the longitudinal axis of elongate member 100, along the portion of elongate member 100 that is located at electrically conductive exposed region 114 of cannula 110 when elongate member 100 is inserted to the pre-determined insertion depth. In this embodiment, when viewed under fluoroscopy, the variation in radiopacity will indicate the location of electrically exposed conductive region 114 substantially along its entire length, thus providing a visual reference for distinguishing the intended location of the lesion.

Figure 3B:
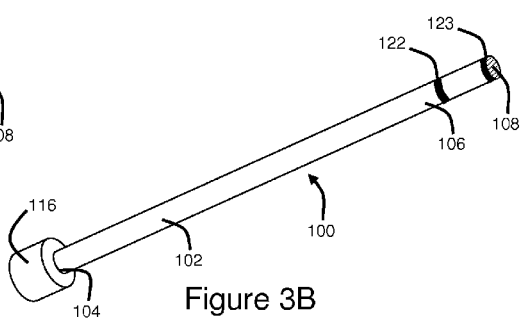

In a further embodiment, as shown in FIG. 3B, two radiopaque markers are used to provide variations in radiopacity at two locations. For example, the first marker 122 may be positioned to substantially longitudinally align with a distal end 120 of the electrically insulated region 112 of cannula 110 when elongate member 100 is inserted to the predetermined insertion depth, and the second marker 123 may be positioned to substantially longitudinally align with the distal end of electrically exposed conductive region 114 of cannula 110 when elongate member 100 is inserted to the predetermined insertion depth. In this embodiment, when viewed under fluoroscopy, the radiopaque markers 122, 123 would provide and/or define a frame for electrically exposed conductive region 114, and thereby would provide a visual reference for distinguishing the intended location of the lesion.

Figure 3C:
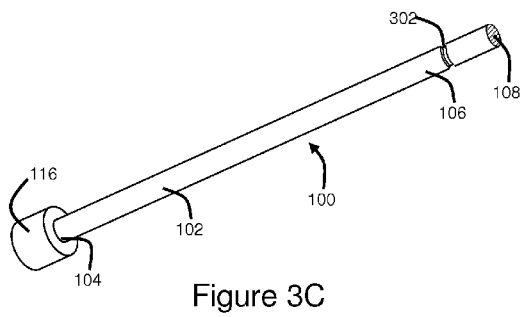
Figure 3D:
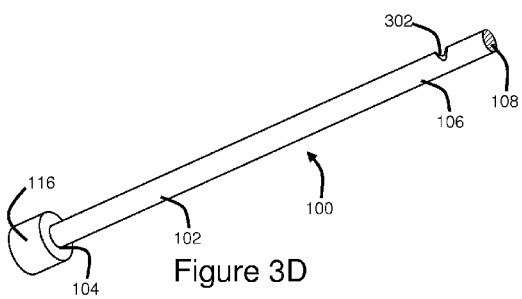

Referring to FIGS. 3C and 3D, in some embodiments, the variation in radiopacity is provided by a reduction in the radiopacity of a portion of elongate member 100. This may be accomplished by removing material from a portion of elongate member 100. For example, elongate member 100 may comprise an indentation 302, which is positioned to substantially longitudinally align with the distal end 120 of electrically insulated region 112 when elongate member 100 is inserted to the predetermined insertion depth. Indentation 302 may be any reduction in material, which, when viewed under fluoroscopy, will appear to have diminished intensity when compared with the remainder of elongate member 100 and cannula 110. For example, indentation 302 may comprise a notch, groove or recess in elongate member 100.

Indentation 302 may substantially circumscribe elongate member 100, as shown in FIG. 3C, or may be located on only a portion of the circumference of elongate member 100, as shown in FIG. 3D. Indentation 302 may be formed by various grinding techniques, or by any other means of removing material. Indentation 302 may be of various widths, wherein 'width' refers to the distance between a proximal edge and a distal edge of indentation 302. For example, in some embodiments, indentation 302 may have a width of between about 1 mm and about 2 mm (approximately 0.04-0.08 inches), more specifically between about 1.2 and about 1.3 mm (approximately 0.045-0.055 inches). In an alternate embodiment, indentation 302 may run parallel to the longitudinal axis of elongate member 100, along the portion of elongate member 100 that is to be located at electrically conductive exposed region 114 of cannula 110.

Referring to FIG. 3E, in some embodiments, proximal region 102 and distal region 106 of elongate member 102 may be of differing radiopacity. Proximal region 102 and distal region 106 are sized such that the boundary 304 between proximal region 102 and distal region 106 substantially longitudinally aligns with the distal end 120 of electrically insulated region 112 when elongate member 100 is inserted to the pre-determined insertion depth. In a first embodiment, proximal region 102 may be made from a material that is substantially more radiopaque than distal region 106. Thus, when viewed under fluoroscopy, proximal region 102 will appear enhanced relative to distal region 106. For example, proximal region 102 may be made from stainless steel, and distal region 106 may be made from a plastic. Alternatively, both of distal region 106 and proximal region 102 may be made from the same material, and proximal region 102 may be coated with a material of higher radiopacity. For example, distal region 106 and proximal region 102 may both be made from stainless steel, and proximal region 102 may be electroplated with platinum. In an alternate embodiment, proximal region 102 may be made from a material that is substantially less radiopaque that distal region 106. Thus, when viewed under fluoroscopy, proximal region 102 will appear with diminished intensity relative to distal region 106. For example, proximal region 102 may be made from a plastic, and distal region 106 may be made from a stainless steel. In these embodiments, the boundary 304 between proximal region 102 and distal region 106 provides the visual reference for distinguishing, using fluoroscopic imaging, the intended location of the lesion.

Referring to FIG. 3F, in some embodiments, distal region 106 may have a larger transverse cross-sectional area than proximal region 102, and proximal region 102 and distal region 106 may be sized such that the boundary 304 between proximal region 102 and distal region 106 substantially longitudinally aligns with the distal end 120 of electrically insulated region 112 when elongate member 100 is inserted to the pre-determined insertion depth. For example, distal region 106 may be sized such that it substantially radially fills the lumen of cannula 110, and proximal region 102 may be sized such that it radially fills only a portion of the lumen of cannula 110. Thus, when viewed under fluoroscopy, proximal region 102 will appear to have diminished intensity relative to distal region 106. In this embodiment, the boundary 304 between proximal region 102 and distal region 106 provides the visual reference for distinguishing, using fluoroscopic imaging, the intended location of the lesion. In an alternate embodiment, distal region 106 may have a smaller transverse cross-sectional area than proximal region 102.

Figure 4:
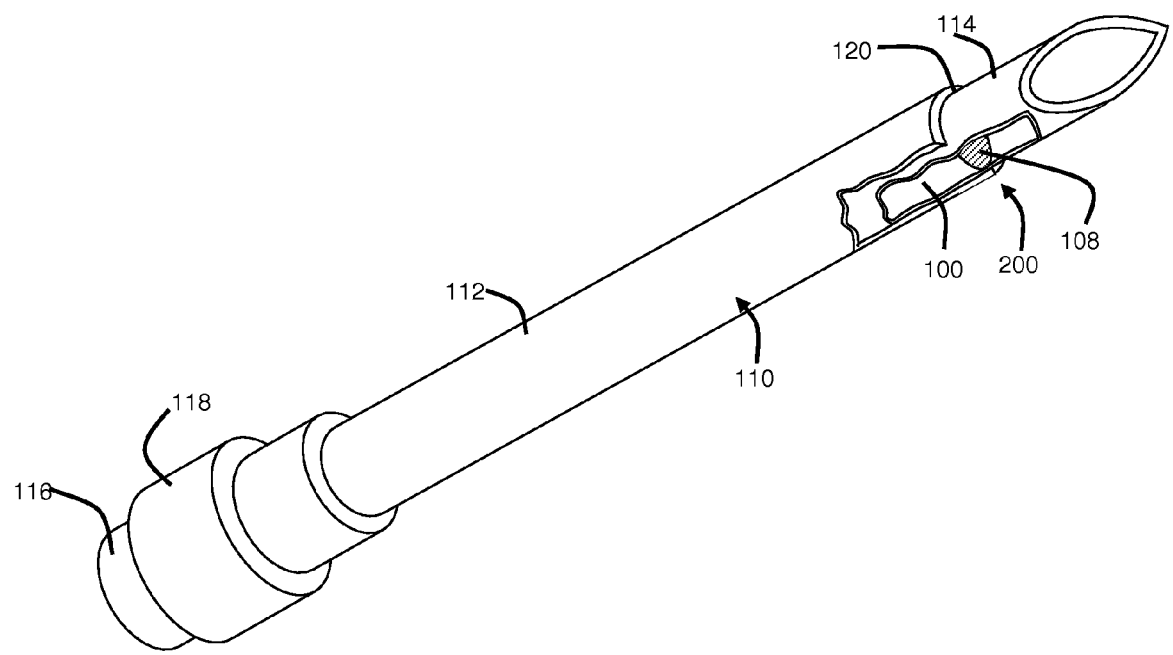
FIG. 4 is a perspective cut-away view a cannula with an alternate embodiment of an elongate member of the present invention inserted into the cannula.

Referring to FIG. 4, in some embodiments, elongate member 100 may be sized such that, when inserted to the pre-determined insertion depth, distal end 108 of elongate member 100 is substantially longitudinally aligned with a distal end 120 of electrically insulated region 112. That is, in some embodiments, elongate member 100 may be substantially shorter than cannula 110, such that when inserted to the pre-determined insertion depth, elongate member 100 does not extend substantially into electrically conductive exposed region 114 of cannula 110. Alternatively, elongate member 100 may not be shorter than cannula 100, but rather, elongate member 100 may be structured such that, when inserted to the predetermined insertion depth, a portion of proximal region 102 may remain outside of cannula 110. This may be accomplished by placing a depth stopper on elongate member 110 to provide the cooperative engagement. This embodiment will be described further hereinbelow with reference to FIG. 7. In these embodiments, wherein distal end 108 of elongate member 100 is substantially longitudinally aligned with a distal end 120 of electrically insulated region 112, when the combined apparatus is viewed under fluoroscopy, electrically insulated region 112 will appear enhanced relative to electrically exposed conductive region 114. Thus, in such embodiments, distal end 108 of elongate member 100 provides the visual reference for distinguishing, using fluoroscopic imaging, the intended location of the lesion.

Figure 5A:
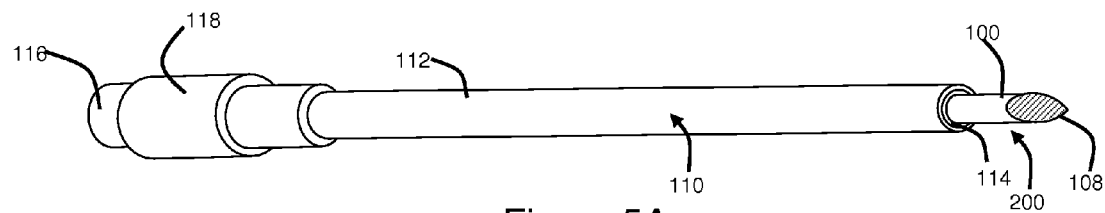
FIG. 5A is a perspective view of another embodiment of an elongate member of the present invention shown inserted into a cannula.
Figure 5B:
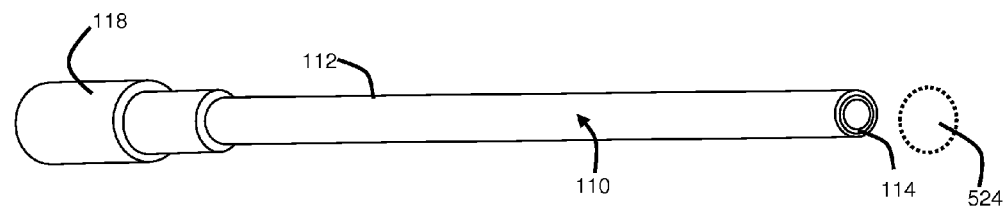
FIG. 5B is a perspective view of the cannula of FIG. 5A, showing the location of a lesion formed therefrom.

Referring to FIGS. 5A and 5B, in some embodiments, cannula 110 may be structured such that electrically insulated region 112 extends to the distal end of cannula 110, and electrically exposed conductive region 114 comprises substantially only the distal face of cannula 110. Although the distal face of cannula 110 is shown in FIGS. 5A and 5B as being flat, it may have other shapes as well, including but not limited to rounded or hemispherical shapes. Furthermore, cannula 110 may be structured such that, during the delivery of energy, at least a portion of cannula 110 is cooled, for example by the insertion of an internally cooled probe into cannula 110. Further details regarding such embodiments are provided in U.S. patent application Ser. No. 11/457,697 (filed on Jul. 14, 2006), previously incorporated herein by reference. In such embodiments, the intended location of the lesion may be located substantially distally relative to electrically exposed conductive region 114, and may or may not contact electrically exposed conductive region 114. In such embodiments, elongate member 100 may be sized such that when it is inserted to the predetermined insertion depth, a portion of distal region 106 of elongate member 100 extends beyond a distal end of cannula 110, to the intended location of the lesion 524. That is, elongate member 100 may be longer than cannula 110. When viewed under fluoroscopy, the portion of elongate member 100 that extends beyond the distal end of cannula 110 will appear to have diminished intensity relative to cannula 102. Thus, in such embodiments, the variation in radiopacity is provided by the portion of distal region 106 of elongate member 100 that extends beyond the distal end of cannula 110. When elongate member 100 is removed from cannula 110, and energy is delivered from cannula 110, lesion 524 will form at the location to which distal region 106 extended. In other words, distal end 108 of elongate member 100 may substantially indicate the location where a lesion will form when energy is delivered from cannula 110.

Figure 6A:
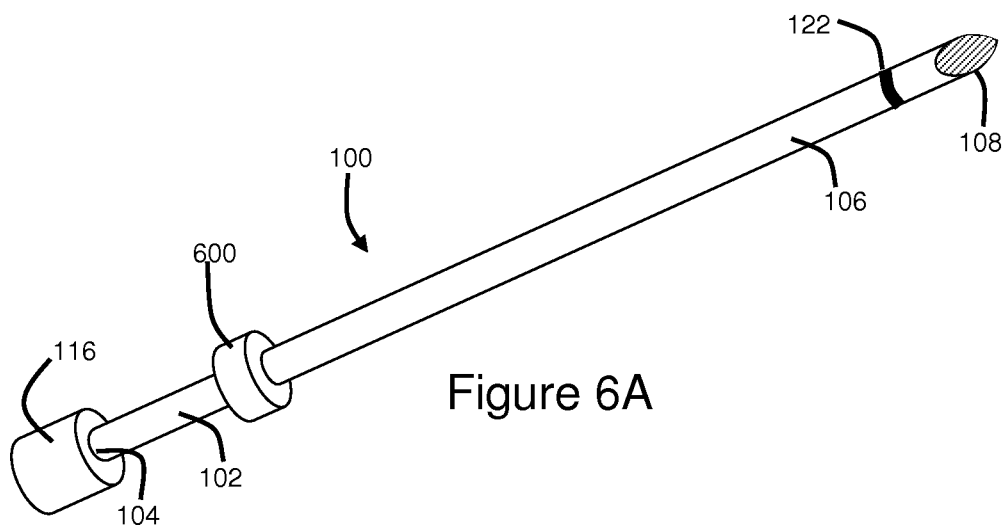
FIG. 6A is a perspective view of an embodiment of an elongate member of the present invention comprising a depth stopper.
Figure 6B:
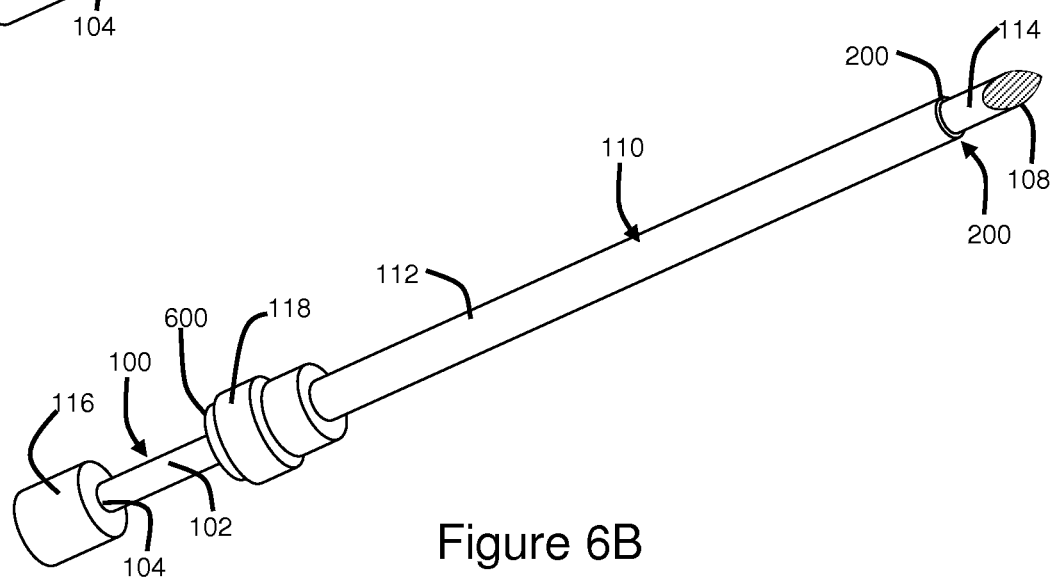
FIG. 6B is a perspective view of the elongate member of FIG. 6A, shown inserted into a cannula.

As mentioned hereinabove, elongate member 100 is structured to cooperatively engage with cannula 110 at a predetermined insertion depth. In some embodiments, as described hereinabove with reference to FIGS. 1 and 2, this cooperative engagement may be provided by a hub 116 at the proximal end of elongate member 100. In other embodiments, this cooperative engagement may be provided by a depth stopper or other means for substantially preventing longitudinal motion of elongate member 100, relative to cannula 110. Referring to FIG. 6A, a depth stopper 600 is shown on elongate member 100. In the embodiments shown, depth stopper 600 is an annular component disposed around elongate member 100, which will contact and abut with hub 118 of cannula 110 when elongate member 100 is inserted to the predetermined insertion depth, as shown in FIG. 6B. In other embodiments, the means for substantially preventing longitudinal motion may be any other structure that, during the insertion of elongate member 100 into cannula 110, will resist further insertion, or indicate to the user that the pre-determined insertion depth has been reached, for example a clip or a clamp.

In some embodiments, the distal end 108 of elongate member 100 may be substantially sharp. For example, distal end 108 may be beveled, as shown in FIGS. 1, 2, and 6. In other embodiments, distal end 108 of elongate member 100 may be substantially blunt, as shown in FIGS. 3 and 4. In other embodiments, other shapes are possible, for example rounded, conical, or trocar, and the invention is not limited in this regard. In some embodiments, as shown in FIG. 1, the distal end of cannula 110 is beveled. In such embodiments, distal end 116 of elongate member 100 may be beveled at the same angle so as to be flush with the distal end of cannula 110 when elongate member 100 is inserted to the predetermined insertion depth.

Elongate member 100 may be manufactured from a number of materials, and the invention is not limited in this regard. Suitable materials include stainless steel, titanium, nitinol, any alloys or combinations thereof, or other materials that may impart varying degrees of flexibility and strength to elongate member 100. In some embodiments, different portions of elongate member 100 may be manufactured from different materials. For example, it the embodiment of FIG. 3E, proximal region 102 may be manufactured from stainless steel, and distal region 106 may be manufactured from polycarbonate.

In some embodiments, cannula 110 may be curved or bent. In such embodiments, elongate member 100 may also be curved or bent, in order fit within the lumen of cannula 110.

An electrosurgical system incorporating an elongate member of the present invention may further comprise any or all of an energy generator, one or more cannulae, for example cannula 110, one or more probes, a reference electrode, one or more occluding members, and electrical connections, for examples wires and/or cables, as described, for example, in U.S. patent application Ser. No. 11/079,318, previously incorporated herein by reference. Typically, high frequency electrical current flows from a generator via electrical connections to a probe and via the probe to an electrically exposed conductive region of the cannula. This delivery of energy may result in electrical stimulation or high frequency heating of tissue in the region around the electrically exposed conductive region.

A method embodiment of the present invention may be particularly useful for precisely positioning an electrosurgical apparatus, where accurate knowledge of the area to be treated is critical. In facet joint denervation, for example, it is critical that certain nerves, for example those of the sympathetic chain, are not damaged during the treatment procedure. A radiofrequency treatment procedure, using an elongate member of the present invention, may be performed as follows: With a patient lying prone on a radiolucent table, a cannula, for example cannula 110, is inserted into the patient's body. In some embodiments, an elongate member, for example elongate member 100, is inserted into the cannula to a pre-determined insertion depth prior to the insertion of the cannula into the patient's body. In such embodiments, the elongate member may substantially occlude the lumen of the cannula, in order to aid in insertion. In other embodiments, the elongate member is inserted into the cannula to a pre-determined insertion depth after the cannula has been inserted into the patient's body. In embodiments wherein the elongate member is inserted into the cannula after the cannula has been inserted into the patient's body, an occluding member, for example a stylet, may be inserted into the cannula prior to the insertion of the cannula into the patient's body. The occluding member may be removed from the cannula after the cannula has been inserted into the patient's body, and the elongate member may then be inserted into the cannula.

Figure 7A:
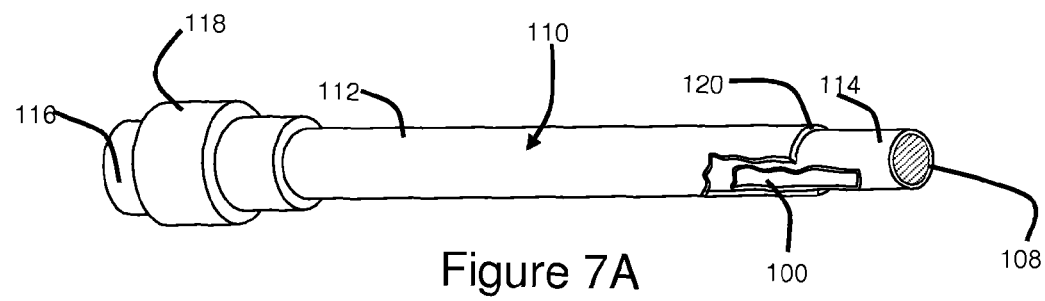
FIG. 7A is a perspective view of an embodiment of an elongate member of the present invention inserted to a first position within a cannula.
Figure 7B:
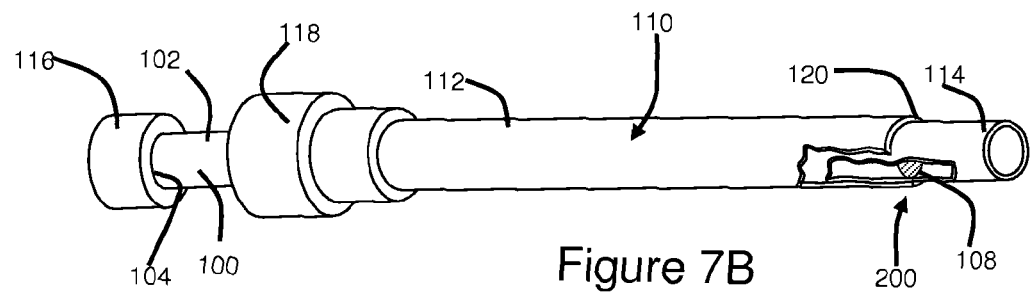
FIG. 7B is a perspective view of the elongate member of FIG. 7A inserted to a predetermined insertion depth within a cannula.

In one particular embodiment, prior to the insertion of the cannula into the patient's body, the elongate member may be inserted into the cannula to a first position, for example as shown in FIG. 7A, whereby at the first position the elongate member substantially occludes the distal end of the cannula for aiding in the insertion of the cannula. The cannula and elongate member may then be inserted into the patient's body to a position near the target location. The elongate member may then be repositioned to the predetermined insertion depth, for example as shown in FIG. 7B, by retracting the elongate member such that the distal end of the elongate member is substantially longitudinally aligned with a distal end of the electrically insulated region, as described hereinabove with reference to FIG. 4. A depth stopper or other means for limiting longitudinal motion may then be placed on the elongate member to maintain the elongate member at the predetermined insertion depth.

When the cannula has been inserted, and with the elongate member inserted to the pre-determined insertion depth, the user may determine the location of the lesion to be made. That is, the elongate member and cannula may be visualized under fluoroscopy, such that the variation in radiopacity provided by the elongate member provides a visual reference for determining the location of the lesion to be made. For example, if the elongate member comprises a radiopaque marker substantially longitudinally aligned with the distal end of the electrically insulated region of the cannula, when viewed under fluoroscopy, the distal end of the electrically insulated region of the cannula will appear enhanced relative to the remainder of the cannula. This enhanced region serves as a visual reference for the user, indicating to the user that the proximal-most region of the lesion will be at the enhanced region visible on the fluoroscopic image.

In some cases, responsive to determining the location of the lesion to be made, the user may determine that it is necessary to move the cannula. For example, the target nerve may not be within the previously determined location of the lesion to be made. Thus, the user may move the cannula to precisely position the electrically exposed conductive region such that at least a portion of the target site is located within the location of the lesion to be made.

Once the cannula is positioned, the elongate member may be removed and replaced by a radiofrequency probe. The location of a target nerve within the target site may be confirmed by sensory stimulation. Finally, following a test for motor stimulation as an added safety measure, energy may be delivered from an energy generator through the probe to the active tip of the cannula in order to create a lesion about the target nerve. In some embodiments of the treatment procedure, anesthetic or other diagnostic or therapeutic agents may be injected through the cannula. The method aspect of the present invention also provides for the insertion of multiple cannulae and multiple elongate members of the present invention over the course of a treatment procedure, whereby any or all of the cannulae and elongate members may be positioned under fluoroscopic guidance, as described herein above. It should be noted that, rather than using a separate probe, energy may be delivered directly to the cannula from the energy generator, for example via one or more wires or cables connected directly to the cannula. Alternatively, the elongate member may be operable to be connected to the energy generator such that energy may be delivered from the energy generator, via the elongate member, to the electrically conductive exposed region of the cannula.

Thus, in one broad aspect, embodiments of the present invention comprise an elongate member for inserting into a cannula. The cannula may comprise an electrically insulated region and an electrically exposed conductive region for delivering energy to form a lesion within a patient's body at an intended location relative to the electrically exposed conductive region. The elongate member is structured to cooperatively engage with the cannula at a pre-determined insertion depth, and to provide a variation in radiopacity at a pre-determined position relative to the electrically exposed conductive region when inserted to the pre-determined insertion depth. The variation in radiopacity provides a visual reference for distinguishing, using fluoroscopic imaging, the intended location of the lesion.

Embodiments of the present invention, as described herein above, allow a user to determine, with greater precision than previously possible, the location where a lesion will be formed during an electrosurgical procedure. This allows the user to more precisely position the cannula to ensure that the target of energy delivery will indeed be encompassed by the lesion. In addition, by associating the variation in radiopacity with a structural feature of the elongate member, as opposed to the cannula, the outer profile of the cannula remains unchanged, such that the force required to insert the cannula within the patient's body is not increased.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An elongate member and cannula assembly, comprising:
a cannula comprising a lumen, an electrically insulated region, and an electrically-exposed conductive region, the lumen extending through the electrically insulated region and the electrically-exposed conductive region, the electrically-exposed conductive region configured for delivering energy to form a lesion within a patient's body at an intended location; and
an elongate member configured within the cannula, the elongate member comprising a proximal region, a distal region, and a pre-determined length, the elongate member engaged with the cannula via a structure at the proximal region such that the pre-determined length extends a pre-determined insertion depth within the cannula and remains fixed therein, the elongate member comprising a non-conductive radiopaque marker at a pre-determined position on an outer surface of the distal region of the of the elongate member,
wherein the radiopaque marker provides a variation in radiopacity at the pre-determined position when the elongate member is engaged with the cannula via the structure and inserted to the pre-determined insertion depth, the pre-determined length of the elongate member being sized such that, when the elongate member is cooperatively engaged with the cannula via the structure and inserted to the pre-determined insertion depth, a distal end of the elongate member extends beyond a distal end of the electrically insulated region of the cannula and aligns with a distal end of the electrically-exposed region of the cannula such that the radiopaque marker aligns with the distal end of the electrically insulated region to indicate the intended location of the lesion, the cannula connectable to an energy source for forming the lesion.

2. The assembly of claim 1, further comprising a second radiopaque marker positioned to align with a distal end of the electrically-exposed conductive region of the cannula when the elongate member is inserted to the pre-determined insertion depth so as to provide a frame for the electrically-exposed conductive region and a visual reference for distinguishing the intended location of the lesion.

3. The assembly of claim 1, wherein the radiopaque marker comprises a platinum band.

4. The assembly of claim 1, wherein the radiopaque marker comprises an indentation in the elongate member, the indentation positioned to align with the distal end of the electrically insulated region when the elongate member is inserted to the pre-determined insertion depth.

5. The assembly of claim 1, wherein the proximal region and the distal region are of differing radiopacity, and the proximal region and the distal region are sized such that a boundary between the proximal region and the distal region aligns with a distal end of the electrically insulated region when the elongate member is inserted to the pre-determined insertion depth for providing the variation in radiopacity.

6. The assembly of claim 1, wherein extension of the distal end of the elongate member beyond a distal end of the cannula provides variation in radiopacity.

7. The assembly of claim 1, wherein the proximal region has a smaller diameter than the distal region, and the proximal region and the distal region are sized such that a boundary between the proximal region and the distal region aligns with a distal end of the electrically insulated region when the elongate member is inserted to the pre-determined insertion depth for providing the variation in radiopacity.

8. The assembly of claim 1, wherein a depth stopper on the elongate member provides the cooperative engagement.

9. The assembly of claim 1, wherein the elongate member further comprises a hub at a proximal end thereof, and the hub provides the cooperative engagement.

10. The assembly of claim 1, wherein the elongate member is manufactured from a material selected from the group consisting of stainless steel, titanium, nitinol, alloys thereof, and any combination thereof.

11. A kit comprising:
a cannula comprising a lumen, an electrically insulated region, and an electrically-exposed conductive region, the lumen extending through the electrically insulated region and the electrically-exposed conductive region, the electrically conductive region configured for delivering energy to form a lesion within a patient's body at an intended location;
an elongate member inserted within cannula, the elongate member having a proximal region, a distal region, and a pre-determined length, the elongate member engaged with the cannula via a structure at the proximal region such that the pre-determined length extends a pre-determined insertion depth within the cannula and remains fixed therein, the elongate member comprising a non-conductive radiopaque marker at a pre-determined position on an outer surface of the distal region of the of the elongate member, wherein the radiopaque marker provides a variation in radiopacity at the pre-determined position when the elongate member is engaged with the cannula via the structure and inserted to the pre-determined insertion depth;

the pre-determined length of the elongate member being sized such that, when the elongate member is cooperatively engaged with the cannula via the structure and inserted to the pre-determined insertion depth, a distal end of the elongate member extends beyond a distal end of the electrically insulated region of the cannula and aligns with a distal end of the electrically-exposed region of the cannula such that the radiopaque marker aligns with the distal end of the electrically insulated region to indicate the intended location of the lesion, the cannula being connectable to an energy source for forming the lesion.

\* \* \* \* \*